US011532387B2

(12) United States Patent
Dandala et al.

(10) Patent No.: US 11,532,387 B2
(45) Date of Patent: Dec. 20, 2022

(54) IDENTIFYING INFORMATION IN PLAIN TEXT NARRATIVES EMRS

(71) Applicant: International Business Machines Corporation, Armonk, NY (US)

(72) Inventors: Bharath Dandala, White Plains, NY (US); Ananya Aniruddha Poddar, White Plains, NY (US); Murthy V. Devarakonda, Peekskill, NY (US)

(73) Assignee: International Business Machines Corporation, Armonk, NY (US)

( * ) Notice: Subject to any disclaimer, the term of this patent is extended or adjusted under 35 U.S.C. 154(b) by 714 days.

(21) Appl. No.: 16/548,443

(22) Filed: Aug. 22, 2019

(65) Prior Publication Data

US 2021/0057068 A1 Feb. 25, 2021

(51) Int. Cl.
*G16H 15/00* (2018.01)
*G06N 20/10* (2019.01)
(Continued)

(52) U.S. Cl.
CPC .............. *G16H 15/00* (2018.01); *G06F 40/30* (2020.01); *G06N 3/08* (2013.01); *G06N 20/10* (2019.01); *G16H 10/60* (2018.01)

(58) Field of Classification Search
CPC ........ G16H 15/00; G16H 10/60; G06N 20/10; G06N 3/08; G06F 40/30
See application file for complete search history.

(56) References Cited

U.S. PATENT DOCUMENTS 9,047,283 B1 * 6/2015 Zhang ................. G06F 16/3346
9,734,297 B2 8/2017 Syeda-Mahmood et al.
(Continued)

FOREIGN PATENT DOCUMENTS

WO WO 99/17223 4/1999
WO WO2018/2002274 A1 11/2018

OTHER PUBLICATIONS

Alemzadeh, Homa et al., "An NLP-Based Cognitive System for Disease Status Identification in Electronic Health Records", Feb. 2017 IEEE EMBS International Conference on Biomedical & Health Informatics (BHI), 4 Pages.
(Continued)

*Primary Examiner* — Jay M. Patel
(74) *Attorney, Agent, or Firm* — Stephen J. Walder, Jr.; Kristofer Haggerty

(57) ABSTRACT

A clinical information extraction and training mechanism is provided for automatically extracting and identifying information in plain text narratives in a set of electronic medical records. The mechanism segments each clinical note in a plurality of clinical notes into one or more identified sections, labels each identified section with an associated tag, and generate a tag data structure utilizing explicitly tagged sequences of sentences and associated tags. The mechanism performs statistical analysis of the identified sections that contain tags identified in the tag data structure to identify one or more valid stop/start conditions; extracts a first set of positive examples of sentences for a selected type of information, and then trains a cognitive system to identify sentences in the plurality of clinical notes that fail to have a tag associated with the selected type using the positive examples of sentences for different types of information.

20 Claims, 7 Drawing Sheets

(51) Int. Cl.
  *G16H 10/60* (2018.01)
  *G06N 3/08* (2006.01)
  *G06F 40/30* (2020.01)

(56) References Cited

U.S. PATENT DOCUMENTS

| | | | | |
|---|---|---|---|---|
| 11,205,157 | B2* | 12/2021 | Ahani | G06F 16/2379 |
| 2014/0278554 | A1* | 9/2014 | Mabotuwana | G16H 15/00 |
| | | | | 705/3 |
| 2015/0066539 | A1 | 3/2015 | Sheffer et al. | |
| 2015/0149461 | A1* | 5/2015 | Aguilar Lemarroy | G06F 16/35 |
| | | | | 707/737 |
| 2016/0154792 | A1* | 6/2016 | Sarikaya | G06F 40/35 |
| | | | | 704/9 |
| 2017/0039188 | A1* | 2/2017 | Allen | G06F 40/169 |
| 2017/0132371 | A1* | 5/2017 | Amarasingham | G06F 40/284 |
| 2017/0235885 | A1* | 8/2017 | Cox | G06F 16/2455 |
| | | | | 705/2 |
| 2017/0300635 | A1* | 10/2017 | Ganesan | G16H 15/00 |
| 2018/0018590 | A1* | 1/2018 | Szeto | G16H 40/20 |
| 2018/0032497 | A1* | 2/2018 | Mukherjee | G06V 30/416 |
| 2018/0060302 | A1* | 3/2018 | Liang | G06F 16/35 |
| 2018/0089382 | A1* | 3/2018 | Allen | G06F 40/295 |
| 2018/0089568 | A1* | 3/2018 | Allen | G06N 5/02 |
| 2018/0121539 | A1* | 5/2018 | Ciulla | G06F 16/3344 |
| 2018/0137090 | A1* | 5/2018 | Duan | G06F 40/30 |
| 2018/0143975 | A1* | 5/2018 | Casal | G06F 40/51 |
| 2018/0173698 | A1* | 6/2018 | Dubey | G06F 16/3347 |
| 2018/0196920 | A1* | 7/2018 | Liang | G16H 10/60 |
| 2018/0322110 | A1 | 11/2018 | Rhodes | |

OTHER PUBLICATIONS

Go, Alec et al., "Twitter Sentiment Classification using Distant Supervision", Technical Report, Stanford University, Jan. 2009, 6 Pages.

Hu, Minqing et al., "Mining and Summarizing Customer Reviews", In Proc. of the 10th ACM SIGKDD International Conference on Knowledge Discovery and Data Mining, Seattle Washington, Aug. 2004, 10 pages.

Kim, Yoon , "Convolutional Neural Networks for Sentence Classification", Proceedings of the 2014 Conference on Empirical Methods in Natural Language Processing (EMNLP), Oct. 2014, Doha, Qatar, 6 Pages.

Krause, Sebastian et al., "Large-Scale Learning of Relation-Extraction Rules with Distant Supervision from the Web", Language Technology Lab, DFKI, Alt-Moabit 91c, Germany, ISWC 2012, Part 1 LNCS 7649, 16 pages.

Liu, Bing , "Sentiment Analysis and Opinion Mining", Synthesis Lectures on Human Language Technologies, Apr. 22, 2012, Published by Morgan & Claypool Publishers, May 2012, 168 Pages.

McCord, M.C. et al., "Deep parsing in Watson", IBM J. Res. & Dev. vol. 56 No. 3/4 Paper3, May/Jul. 2012, pp. 3:1-3:15.

Mintz, Mike et al., "Distant supervision for relation extraction without labeled data", Proceedings of the 47th Annual Meeting of the ACL and the 4th IJCNLP of the AFNLP, Suntec, Singapore, Aug. 2009, 9 Pages.

Pang, Bo et al., "A Sentimental Education: Sentiment Analysis Using Subjectivity Summarization Based on Minimum Cuts", ACL 2004 Proceedings of the 42nd Annual Meeting on Association for Computational Linguistics, Barcelona, Spain, Jul. 2004, 8 Pages.

Pang, Bo et al., "Seeing stars: Exploiting class relationships for sentiment categorization with respect to rating scales", ACL 2005 Proceedings of the 43rd Annual Meeting on Association for Computational Linguistics, Ann Arbor, Michigan, Jun. 2005.

Pang, Bo et al., "Thumbs up? Sentiment Classification using Machine Learning Techniques", EMNLP, 2002, 8 pages.

Sidorov, Grigori et al., "Syntactic Dependency-Based N-grams: More Evidence of Usefulness in Classification", CICLing 2013, Part 1, LNCS 7816, 2013, 12 Pages.

Wachter, Robert, "The Digital Doctor: Hope, Hype, and Harm at the Dawn of Medicine's Computer Age", McGraw-Hill, (2014), 352 pages.

Wang, Sida et al., "Fast dropout training", Proceedings of the 30th International Conference on Machine Learning, PMLR 28(2):, Jun. 2013, Atlanta, Georgia, 9 Pages.

Wiebe, Janyce et al., "Annotating Expressions of Opinions and Emotions in Language", Language Resources and Evaluation, vol. 39, No. 2-3, 2005, 54 pages.

* cited by examiner

*FIG. 6*

OFFICE VISIT: February, 27, 2014
Patient Name: George W. Smith

PCP: Stanley Welby, MD

HPI: Feeling Fine. Brought a home BP device and checks it periodically. Finds it varies a lot. Can be as high as 150/95 or low as 135/90. Pretty good about his meds.
...

ASSESSMENT:
1. HTN -- started taking home BPs sporadically. Running 135-150/90-95. Admits to not taking his meds consistently. [Have reinforced the importance of controlling his BP due to the cumulative risks for CV events.] I explained how to use the feedback from his BP device to help reinforce the importance of his taking his med regularly. Patient agrees and says he will start taking his BPs regularly and taking his meds.

P: 1. Check home BPs daily; report repeated BPs over 140/90
    2. Reinforce importance of taking meds consistently
    3. May increase meds if home BPs consistently elevated when he is taking his meds regularly
    4. RTC 3 mo 2. Smoking -- talked to patient about the conbiamtion of smoking and HTN and his risk of MI, stroke. Encouraged him to follow his wife's advice about joining the smoking cessation class. Enroll in smoking cessation class.

3. Hyperlipidemia -- will check LDL. Has been under control in the past.
[Plan: Lipid panel.]

IDENTIFYING INFORMATION IN PLAIN TEXT NARRATIVES EMRS

BACKGROUND

The present application relates generally to an improved data processing apparatus and method and more specifically to computer mechanisms for training supervised machine learning models to automatically identify information in plain text narratives of electronic medical records.

Decision-support systems exist in many different industries where human experts require assistance in retrieving and analyzing information, such as from patients' electronic medical records (EMRs). Clinical notes, such as plain text narratives created by clinicians (i.e. physicians, nurses, and other care providers), are a rich source of patient care documentation in the patients' EMRs. While the clinical notes are free-form in principle, clinicians write them using the SOAP (subjective, objective, assessment, and plan) format. Typically, clinicians organize content within the clinical notes using section tags, such as "Assessment:" or "Plan:". For example, the former indicates subsequent text (usually written in multiple lines, sometimes as a bulleted or numbered list) is the clinical assessment and the latter indicates a treatment plan. However, the presence of such tags is not guaranteed and their surface representation may vary considerably. For example, some clinical notes may use the abbreviated form "P:" or synonymous labels such as "Recommendation:" to indicate treatment plans.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a clinical information extraction and training mechanism for automatically extracting and identifying information in plain text narratives in a set of electronic medical records. The illustrative embodiment segments each clinical note in a plurality of clinical notes into one or more identified sections using natural language processed plain text narratives of the plurality of clinical notes. The illustrative embodiment labels each identified section with an associated tag through a set of sequential steps. The illustrative embodiment generates a tag data structure utilizing explicitly tagged sequences of sentences and associated tags. The illustrative embodiment performs statistical analysis of the identified sections in the plurality of clinical notes that contain tags identified in the tag data structure to identify one or more valid stop/start conditions utilizing the tag data structure. The illustrative embodiment extracts a first set of positive examples of sentences for a selected type of information using associated tags in the tag data structure and the one or more valid stop/start conditions. The illustrative embodiment trains a cognitive system to identify sentences in the plurality of clinical notes that fail to have a tag associated with the selected type using the positive examples of sentences for different types of information.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 6 illustrates an example of a clinical note where treatment plans with and without tags are identified in accordance with one illustrative embodiment.

DETAILED DESCRIPTION

Figure 1:
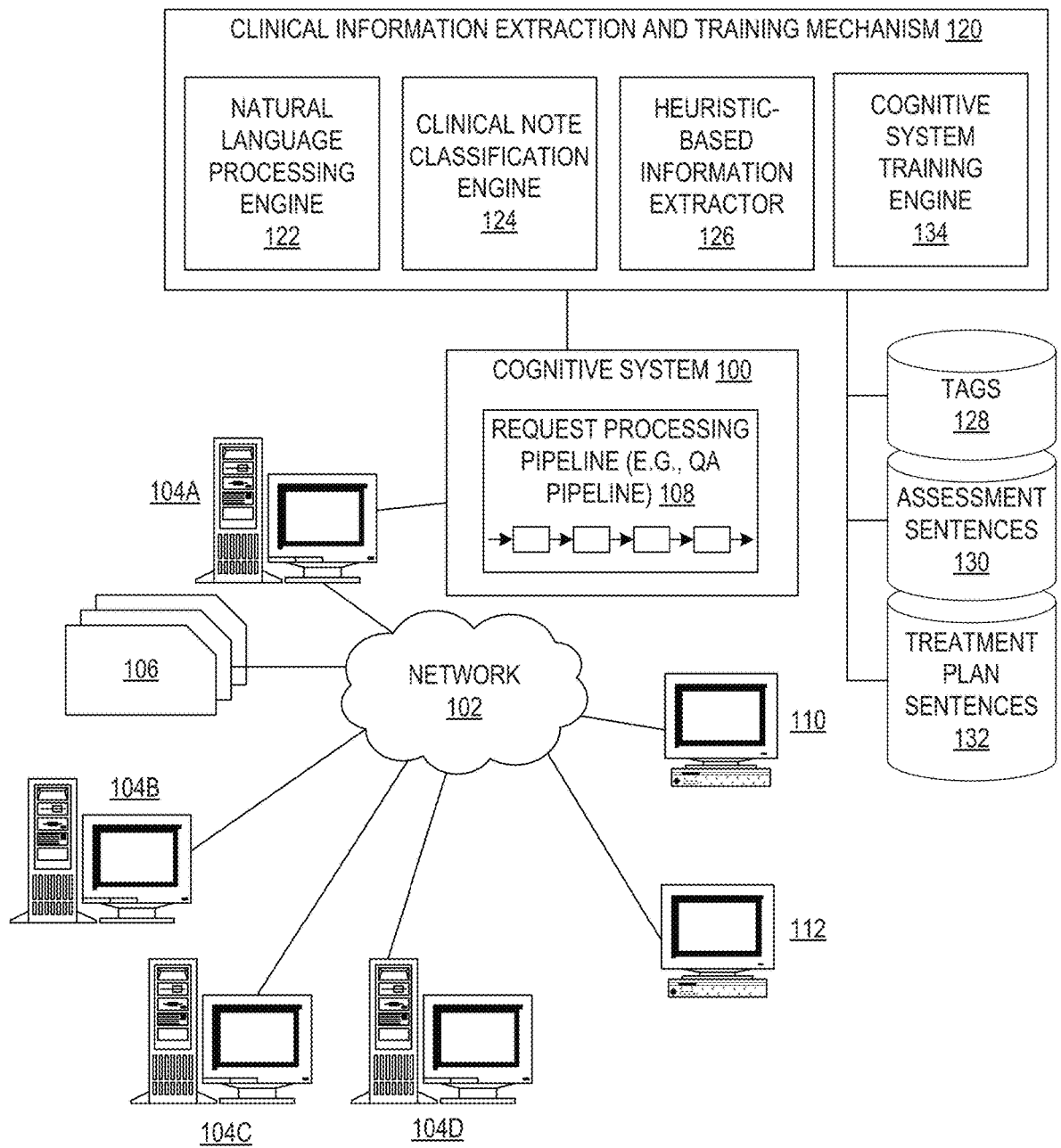
FIG. 1 depicts a schematic diagram of one illustrative embodiment of a cognitive healthcare system in a computer network.

Clinical notes are plain text narratives created by clinicians (i.e. physicians, nurses, and other care providers) in patients' electronic medical records (EMRs). Extracting and succinctly presenting categorical information from such clinical notes has the potential to improve patient care by reducing the need for foraging in a large patient record for critical insights. Previous approaches to extracting information from patients' EMRs are represented by rule-based and machine learning techniques. Rule-based techniques have the advantages of being declarative, easy to comprehend, and easy to incorporate domain knowledge. However, rule-based techniques suffer from some critical disadvantages such as being heuristic and requiring tedious manual labor in building the rules. While in recent years machine learning techniques have been utilized to build effective information extraction models, despite their high performance, these machine learning systems have an important drawback: their applicability is limited to those tasks for which labelled data is available and their accuracy is strongly connected to the amount of labelled data available at hand. In order to address the deficiencies of current machine learning techniques, labeled data was manually created. However, manually creating labelled data is a time-consuming and tedious process. To address this issue, automatic data extraction was added, with the most common efforts in the area of sentiment analysis using online product or service reviews. The reviews were typically accompanied by a predefined "star" rating, which was used as the ground truth to learn sentiment rating from the text.

Thus, although the use of automatically generated training data is currently employed, any ground truth associated with the automatically generated training data was predefined. Thus, the illustrative embodiments provide for automatically generating ground truth from clinical notes to identify information in the clinical notes, such as assessments, treatment plans, or the like. In general, clinical notes are freeform in principle, although, clinicians are trained to write them in a certain generally accepted format and to include certain required content. Typically, the clinicians organize the content using section tags, such as "Assessment:" or "Plan:". For example, the former indicates subsequent text (usually written in multiple lines, sometimes as a bulleted or numbered list) is the clinical assessment and the latter indicates a treatment plan. However, the presence of such tags is not guaranteed and their surface representation may vary considerably. For example, some notes may use the abbreviated form "P:", or synonymous labels such as "Recommendation:" to indicate treatment plans. The tagged sections when present can serve as a source of high precision training data because the tag and simple additional rules may be leveraged to extract the sentences within the scope of the tag. These extracted sentences may be used as positive and negative instances to train a supervised machine learning model, which later could recognize sentences belonging to the same category occurring without the tag elsewhere in the same clinical note or in other clinical notes. Thus, the illustrative embodiments provide for automatically extracting training data from clinical notes that leverages section tags and then leverages such data to train supervised machine learning models which helps to automatically identify information in the plain text narratives of patients' EMRs, such as assessments, treatment plans, or the like.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for training supervised machine learning models to automatically identify information in plain text narratives of patients' electronic medical records (EMRs), such as assessments, treatment plans, or the like. Using clinical notes, tagged sections from clinical notes serve are utilized as a source of high-precision training data to extract the sentences within the scope of the tag. These extracted sentences are then utilized as positive instances to train supervised machine learning models, which in turn are utilized to recognize information occurring without the tag elsewhere in the same clinical note or in other clinical notes.

The illustrative embodiments may be utilized in many different types of data processing environments. In order to provide a context for the description of the specific elements and functionality of the illustrative embodiments, FIGS. 1-5 are provided hereafter as example environments in which aspects of the illustrative embodiments may be implemented. It should be appreciated that FIGS. 1-5 are only examples and are not intended to assert or imply any limitation with regard to the environments in which aspects or embodiments of the present invention may be implemented. Many modifications to the depicted environments may be made without departing from the spirit and scope of the present invention.

FIGS. 1-5 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for extracting sentences from clinical notes based on tagged sections from the clinical notes serve that are utilized as a source of high-precision training data. These extracted sentences are then utilized as positive instances to train supervised machine learning models, which in turn are utilized to recognize information occurring in the same clinical note or in other clinical notes that fail to have an associated tag.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to medical assessments while another request processing pipeline may be trained to answer input requests directed to medical treatment plans. In other cases, for example, the request processing pipelines may be configured to provide different types of cognitive functions or support different types of healthcare applications, such as one request processing pipeline being used for patient diagnosis, another request processing pipeline being configured for medical treatment recommendations, another request processing pipeline being configured for patient monitoring, etc.

Moreover, each request processing pipeline may have their own associated corpus or corpora that they ingest and operate on, e.g., one corpus for blood disease domain documents and another corpus tor cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to utilize mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What treatment plans applies to patient P?", the cognitive system may instead receive a request of "identify treatment plans for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to training supervised machine learning models to automatically identify information in plain text narratives of electronic medical records, such as assessments, treatment plans, or the like.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-5 are only examples and are not intended to state or imply any limitation with regard to the type of cognitive system mechanisms with which the illustrative embodiments are implemented. Many modifications to the example cognitive system shown in FIGS. 1-5 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operations(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding
Ingest and process vast amounts of structured and unstructured data
Generate and evaluate hypothesis
Weigh and evaluate responses that are based only on relevant evidence
Provide situation-specific advice, insights, and guidance
Improve knowledge and learn with each iteration and interaction through machine learning processes
Enable decision making at the point of impact (contextual guidance)
Scale in proportion to the task
Extend and magnify human expertise and cognition
Identify resonating, human-like attributes and traits from natural language
Deduce various language specific or agnostic attributes from natural language
High degree of relevant recollection from data points (images, text, voice) (memorization and recall)
Predict and sense with situational awareness that mimic human cognition based on experiences
Answer questions based on natural language and specific evidence In one aspect, cognitive systems provide mechanisms for answering questions posed to these cognitive systems using a Question Answering pipeline or system (QA system)) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data, Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that, the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input, from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. Thus, in accordance with the illustrate embodiment, the corpus or corpora of data 106 may be electronic medical records (EMRs) for a plurality of patients. Each document may include any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. The pipeline 108 will be described in greater detail hereafter with regard to FIG. 5.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, which include clinical notes, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment identification system that analyzes patients' EMRs to automatically identify information in plain text narratives of electronic medical records utilizing supervised machine learning models trained to identify such information with or without tagged sections.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a clinical information extraction and training mechanism for training supervised machine learning models to automatically extract and identify information in plain text narratives of electronic medical records. Clinical information extraction and training mechanism 120 comprises natural language processing engine 122, clinical note classification engine 124, heuristic-based information extractor 126, and cognitive system training engine 134.

In order to initially train cognitive system 100 to identify and extract information in plain text narratives of electronic medical records (EMRs), such as those in the corpus or corpora of data 106, natural language processing engine 122 performs natural language processing, such as sentence segmentation, tokenization, parts-of-speech tagging, parsing, or the like, on the text within each clinical note associated with the EMRs of patients within the corpus or corpora of data 106 so as to link terms in the clinical notes to concepts in language data such as the Unified Medical Language System (UMLS).

Clinical note classification engine 124 then segments the clinical notes into sections and labels each section in a set of sequential steps using one or more different supervised machine learning models. Initially, a section-header identification (supervised learning) model predicts whether a given sentence is the header of a section using several textual and structural features. Subsequently, a section segmentation model segments the clinical note into contiguous blocks of sentences using conditional random fields. The section segmentation model uses predictions from the section-header identifier as a feature. Finally, a section labeler model performs a supervised multi-label classification to assign section labels to the segmented blocks of text.

Heuristic-based information extractor 126 then operates on the sections identified by clinical note classification engine 124. Heuristic-based information extractor 126 utilizes a set of patterns and rules to determine a potential start and a potential end of an explicitly tagged sequence of sentences. The illustrative embodiments consider a contiguous block of sentences as a section, i.e. an assessment section, a treatment plan section, or the like. To develop the set of patterns and rules, heuristic-based information extractor 126 inspects the corpus or corpora of data 106 to identify frequently occurring section headings, such as "Assessment," "A," "Plan," "P," "Recommendation," "Instruction," or the like. Heuristic-based information extractor 126 identifies tags that, when leveraged, yield high precision sentences that serve as positive instances of sentences, i.e.

assessment sentences, treatment plan sentences, or the like, for use in identifying assessments, treatment plans, or the like, that occur in clinical notes but, fail to have identifying tags. Heuristic-based information extractor 126 adds the identified tags to tag data structure 128.

Utilizing tag data structure 128, heuristic-based information extractor 126 performs statistical analysis of all clinical note sections of the clinical notes that contain tags identified in tag data structure 128 to identify one or more valid stop/start conditions. The sections are typically expressed on a malady basis, starting with, for example, a set of assessment sentences followed by a set of treatment plan sentences, which were often written as a list. Therefore, at, the end of such a list, the start of another section may be identified by a section heading of a new malady, a start of a new section identified by clinical note classification engine 124, or a presence of one or more blank lines identifying a robust stop/start condition.

Thus, utilizing the tags in tag data structure 128 as well as the one or more valid stop/start conditions, heuristic-based information extractor 126 extracts positive examples of sentences for different types of information. For example, for assessments within the clinical notes, heuristic-based information extractor 126 identifies assessments sections of the clinical notes identified with an assessment tag, such as "Assessment," "A," or the like. Heuristic-based information extractor 126 extracts the sentences associated with such assessment tags and stores them as positive examples of assessment sentences in assessment sentence data structure 130. As another example, for treatment plans in the clinical notes, heuristic-based information extractor 126 identifies treatment plan sections of the clinical notes identified with a treatment plan tag, s such as "Plan," "P," "Recommendation," "Instruction," or the like. Heuristic-based information extractor 126 extracts the sentences associated with such treatment plan tags and stores them as positive examples of treatment plan sentences in sentence data structure 132. In the illustrative embodiments, while assessment sentences in assessment sentence data structure 130 are examples of positive assessment sentences, these assessment sentences may also be utilized as examples of negative treatment plan sentences. That is, as will be discussed in detail hereafter, in training cognitive system 100 to identify treatment plans that fail to have an associated treatment plan tag, heuristic-based information extractor 126 may utilize those assessment sentences in assessment sentence data structure 130 as negative examples when identifying treatment plan sentences that fail to have an associated treatment plan tag. It should be noted that heuristic-based information extractor 126 may identify other examples of non-treatment plan sentences in clinical notes, such as those that conic from other sections that are identified by other tags associated with other non-treatment plan sections. Heuristic-based information extractor 126 may store these other examples in a different data structure, which is not illustrated in FIG. 1.

With both positive and negative examples of information sentences identified based on associated tags, cognitive system training engine 134 then utilizes the positive and negative examples of information sentences to train cognitive system 100 to classify sentences within clinical notes of the EMRs in the corpus or corpora of data 106 that are identified by tags as well as those that fail to have an associated tag. As one example, cognitive system training engine 134 may be used to classify treatment plan sentences within the clinical notes of the EMRs of a selected patient that are identified by treatment plan tags, such as "Plan," "P," "Recommendation," "Instruction," or the like, as well as those treatment plan sentences that fail to have an associated treatment plan tag. A treatment plan is a therapeutic strategy detailing the treatment to be provided and expected outcome, patient goals, dietary adjustment, an exercise program or expected duration of the treatment prescribed by the clinician, such as a physician, physician assistant, nurse, or the like. Treatment plans are especially important in the optimal management of complex or chronic illnesses. Therefore, identifying each and every treatment plan for the selected patient is important when continuing the healthcare of the patient.

Thus, cognitive system training engine 134 trains cognitive system 100 to classify sentences within clinical notes of the EMRs in the corpus or corpora of data 106 identified by NLP engine 122 utilizing machine learning features such as Support Vector Machines (SVM), Convolutional Neural Networks (CNN), or the like, for identification and classification of sentences within clinical notes of the EMRs in the corpus or corpora of data 106

Utilizing Support Vector Machines, cognitive system training engine 134 sentences train cognitive system 100 to classify sentences not identified by the selected set of tags using the positive examples of the selected information sentences, negative examples of the non-selected information sentences and one or more of the following:

Bag-of-words: A sentence was represented as a set of words and all words in the sentence were lemmatized, i.e. the words of the sentence grouping inflected or variant forms of the same word.

Syntactic n-gram features: Using a medical domain-adapted English Slot Grammar parser to obtain a dependency based syntactic tree for the sentences. Based on the dependency-parse tree provided by the parser, obtaining possible paths of lengths, 2, 3, 4 and include them as features.

Medical concepts: Identify Unified Medical Language System (UMLS) concepts (Concept Unique Identifiers) in a sentence as features.

Morpho-syntactic features of the verbs: Identify features derived from the morpho-syntactic properties of verbs in the sentences. The primary properties and distinctions included the position of the verb (i.e. head of a main clause or an auxiliary, which marks tense and aspect) and the tense markings themselves (past, present or future). Features considered important in identifying treatment plan sentences as they are typically expressed using future tense or imperative verbs. (Example: The patient will be sent for an MRI to further evaluate the knee). On the other hand, an assessment sentences are typically written using past tense verbs. (Example: The patient was able to go through PT but at a much slower pace).

Assertions: identify clinical assertions on medical concepts. Specifically, adding negated and hypothetical assertions on clinical concepts as features. Features considered useful as disease assessments often have negations. (Example: No significant changes since the prior exam). Whereas, treatment plans often contain hypotheticals (Example: Call back if symptoms persist or worsen)

Sentence Length: Information, such as treatment plans, are expressed as multiple short sentences.

Global Features: Utilizing section-labels identified using note section classifiers (introduced earlier), note type (progress note, discharge note etc.), note category (primary care, test reports, specialty category etc.), and provider type (physician, social worker, registered nurse practitioner etc.) as features Therefore, cognitive system training engine 134 trains cognitive system 100 to classify sentences not identified by the selected set of tags using the positive examples of the selected information sentences, negative examples of the non-selected information sentences and one or more of these features. However, the illustrative embodiments may decide which of the features to use in training cognitive system 100 using a statistical feature selection technique, such as Pointwise Mutual Information (PMI), Fisher exact test, or the like.

Cognitive system training engine 134 may also use convolutional neural networks (CNN) that utilizes layers with convolving filters that are applied to local features. In the use of CNN, an embedding layer maps every word with its corresponding low dimensional feature vector. Word vectors may be randomly initialized the embedding layer or initialized with word vectors obtained by training an unsupervised neural language model on a large domain-dependent corpus is effective, in the convolutional neural network architecture, the embedding layer is followed by a convolution layer of different filter sizes, a 1-max pooling layer, a fully connected feed forward neural network layer, and a softmax classifier as the output layer. Global features' embeddings are then concatenated with the outputs of max-pool layer from the word-level inputs. It is worth noting that global features are not at word-level but at sentence-level and they are not sequential like words, thus are not feed in directly at the word-level input layer.

Thus, cognitive system training engine 134 may train cognitive system 100 using convolutional neural networks, such as one or more of:
Utilizing randomly initialized word vectors in the embedding
Utilizing pre-trained word vectors from various articles.
Utilizing pre-trained word vectors from the patients EMRs.
Utilizing pre-trained word vectors from various articles, pre-trained word vectors from the patients EMRs, and selected global features.

Thus, cognitive system training engine 134 may train cognitive system 100 using convolutional neural networks where augment word level features are initialized using pre-trained embeddings and global features initialized using random embedding's in a novel architecture. This word level embeddings and global embedding's are concatenated after the max-pool layer from the word-level inputs. It is worth noting that global features are not at word-level but at sentence-level and they are not sequential unlike words and thus, cannot be feed directly at the word-level input layer.

FIG. 6 illustrates an example of a clinical note where treatment plans with and without tags are identified in accordance with one illustrative embodiment. In this Figure, treatment plans 602 and 604 are identifiable by treatment plan tags, such as "P" and "Plan." However, as illustrated, since treatment plans 606 and 608 fail to be annotate with treatment plan tags, such as "Plan," "P," "Recommendation," "Instruction," or the like, these treatment plans would normally go unrecognized. However, utilizing the mechanisms of the illustrative embodiment, the cognitive system training engine trains a cognitive system to identify treatment plans that fail to be annotate with treatment plan tags using positive instances of treatment plan sentences tagged with treatment plan tags as well as negative instance of other sentences associated with assessments, general data, or the like.

Thus, the illustrative embodiments provide for automatically generating ground truth from clinical notes to identify information in the clinical notes, such as assessments, treatment plans, or the like. The tagged sections serve as a source of high precision training data because the tag and simple additional rules may be leveraged to extract the sentences within the scope of the tag. These extracted sentences may be used as positive and negative instances to train a supervised machine learning model, which are later utilized to recognize sentences belonging to the same category occurring without the tag elsewhere in the same clinical note or in other clinical notes.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above.

It is understood in advance that although this disclosure includes a detailed description on cloud computing, implementation of the teachings recited herein are not limited to a cloud computing environment, Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in, To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources Where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 2:
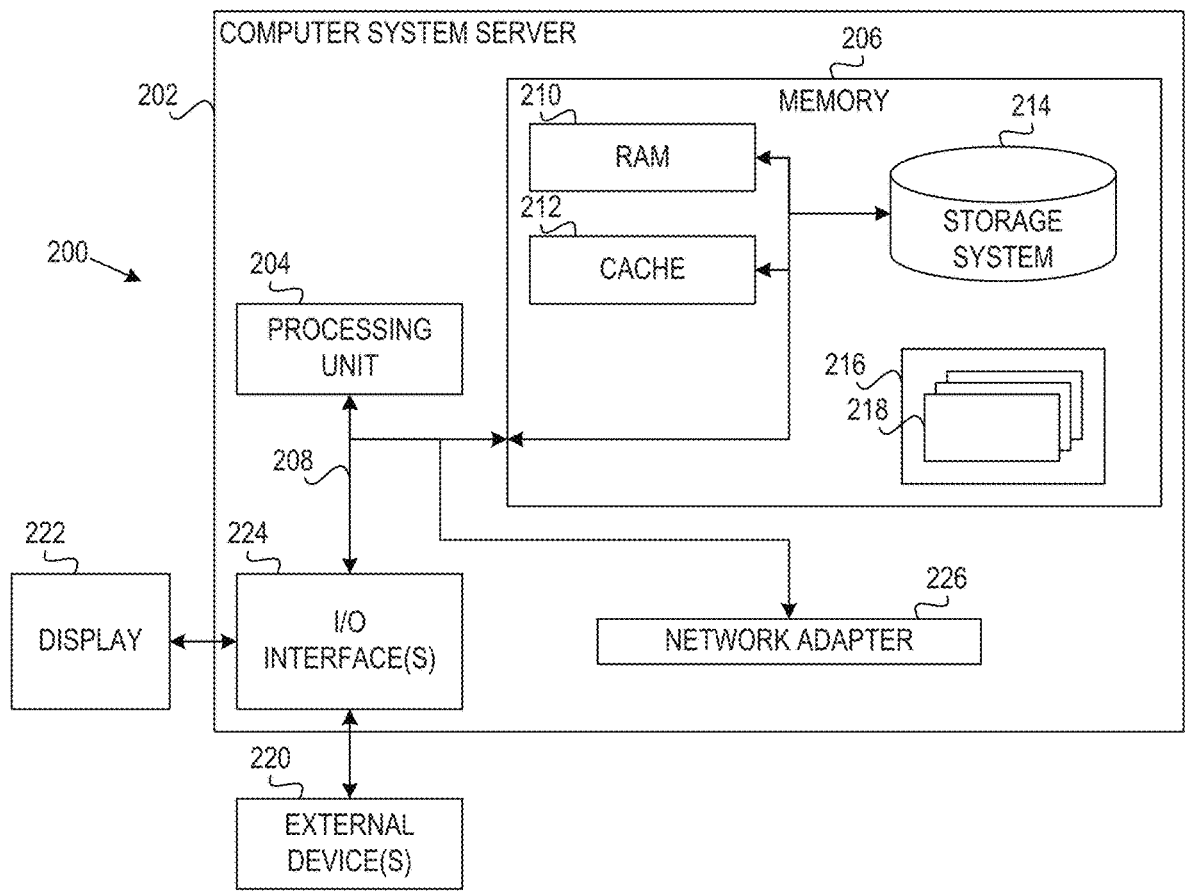
FIG. 2 depicts a cloud computing node according to an embodiment of the present invention.

Referring now to FIG. 2, a schematic of an example of a cloud computing node is shown. Cloud computing node 200 is only one example of a suitable cloud computing node and is not intended to suggest any limitation as to the scope of use or functionality of embodiments of the invention described herein. Regardless, cloud computing node 200 is capable of being implemented and/or performing any of the functionality set forth hereinabove.

In cloud computing node 200 there is a computer system/server 202, which is operational with numerous other general purpose or special purpose computing system environments or configurations. Examples of well-known computing systems, environments, and/or configurations that may be suitable for use with computer system/server 202 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 202 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 202 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 2, computer system/server 202 in cloud computing node 200 is shown in the form of a general-purpose computing device. The components of computer system/server 202 may include, but are not limited to, one or more processors or processing units 204, a system memory 206, and a bus 208 that couples various system components including system memory 206 to processor 204.

Bus 208 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 202 typically includes a variety of computer system readable media. Such media may be any available media that is accessible by computer system/server 202, and it includes both volatile and non-volatile media, removable and non-removable media.

System memory 206 can include computer system readable media in the form of volatile memory, such as random access memory (RAM) 210 and/or cache memory 212. Computer system/server 202 may further include other removable/non-removable, volatile/non-volatile computer system storage media. By way of example only, storage system 214 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 208 by one or more data media interfaces. As will be further depicted and described below, memory 206 may include at least one program product having a set (e.g., at least one) of program modules that are configured to carry out the functions of embodiments of the invention.

Program/utility 216, having a set (at least one) of program modules 218, may be stored in memory 206 by way of example, and not limitation, as well as an operating system, one or more application programs, other program modules, and program data. Each of the operating system, one or more application programs, other program modules, and program data or some combination thereof, may include an implementation of a networking environment. Program modules 218 generally carry out the functions and/or methodologies of embodiments of the invention as described herein.

Computer system/server 202 may also communicate with one or more external devices 220 such as a keyboard, a pointing device, a display 222, etc.; one or more devices that enable a user to interact with computer system/server 202; and/or any devices (e.g., network card, modem, etc.) that enable computer system/server 202 to communicate with one or more other computing devices. Such communication can occur via Input/Output (I/O) interfaces 224. Still yet, computer system/server 202 can communicate with one or more networks such as a local area network (LAN), a general wide area network (WAN), and/or a public network (e.g., the Internet) via network adapter 226. As depicted, network adapter 226 communicates with the other components of computer system/server 202 via bus 208. It should be understood that although not shown, other hardware and/or software components could be used in conjunction with computer system/server 202. Examples, include, but are not limited to: microcode, device drivers, redundant processing units, external disk drive arrays, RAID systems, tape drives, and data archival storage systems, etc.

Figure 3:
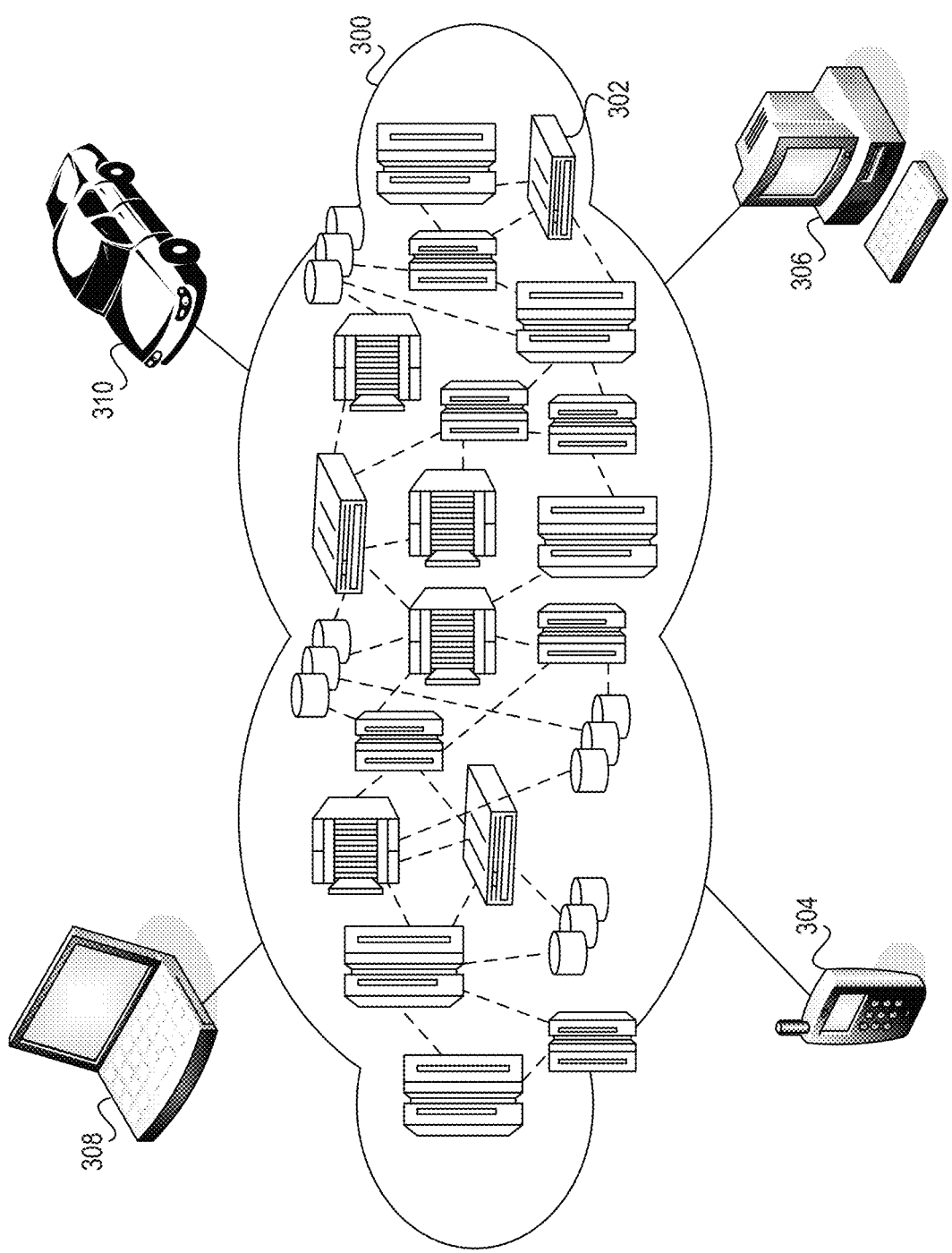
FIG. 3 depicts a cloud computing environment according to an embodiment of the present invention.

Referring now to FIG. 3, illustrative cloud computing environment 300 is depicted. As shown, cloud computing environment 300 comprises one or more cloud computing nodes 302 with which local computing devices used by cloud consumers, such as, for example, personal digital assistant (PDA) or cellular telephone 304, desktop computer 306, laptop computer 308, and/or automobile computer system 310 may communicate. Nodes 302 may communicate with one another. They may be grouped (not shown) physically or virtually, in one or more networks, such as Private, Community, Public, or Hybrid clouds as described hereinabove, or a combination thereof. This allows cloud computing environment 300 to offer infrastructure, platforms and/or software as services for which a cloud consumer does not need to maintain resources on a local computing device. It is understood that the types of computing devices 304, 306, 08, and 310 shown in FIG. 3 are intended to be illustrative only and that computing nodes 302 and cloud computing environment 300 can communicate with any type of computerized device over any type of network and/or network addressable connection (e.g., using a web browser).

Figure 4:
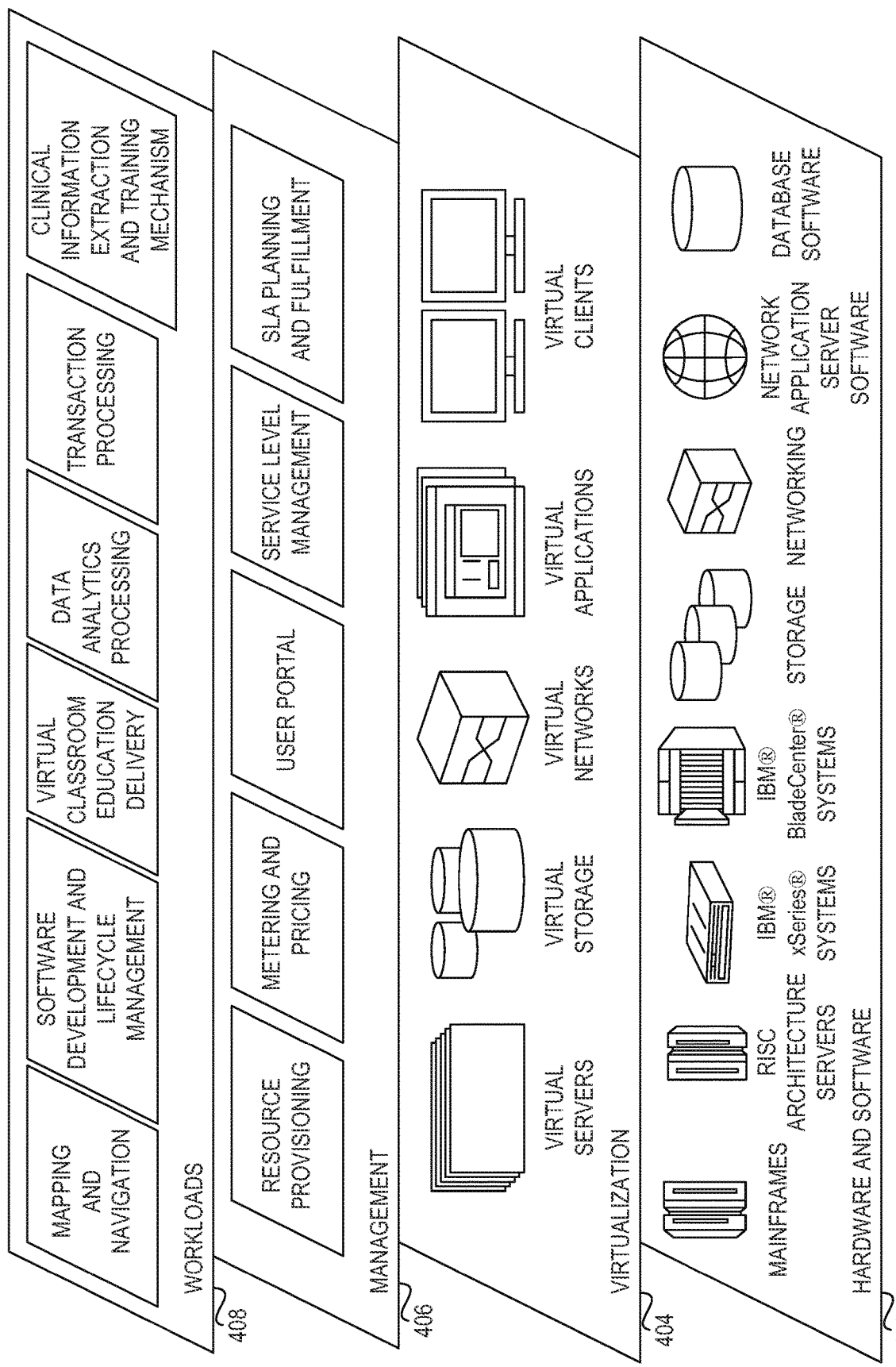
FIG. 4 depicts abstraction model layers according to an embodiment of the present invention.

Referring now to FIG. 4, a set of functional abstraction layers provided by cloud computing environment 300 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 402 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 404 provides an abstraction layer from which the following examples of virtual entities may be provided: virtual servers; virtual storage; virtual networks, including virtual private networks; virtual applications and operating systems; and virtual clients.

In one example, management layer 406 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer 408 provides examples of functionality for which the cloud computing environment may be utilized. Examples of workloads and functions which may be provided from this layer include: mapping and navigation; software development and lifecycle management; virtual classroom education delivery; data analytics processing; transaction processing; and clinical information extraction and training mechanism.

As mentioned above, the cognitive system 100 may include a request processing pipeline, such as request processing pipeline 108 in FIG. 1, Which may be implemented, in some illustrative embodiments, as a Question Answering (QA) pipeline. The QA pipeline may receive an input question, such as "What treatment plans applies to patient P?", or a request, such as "identify treatment plans for patient P."

Figure 5:
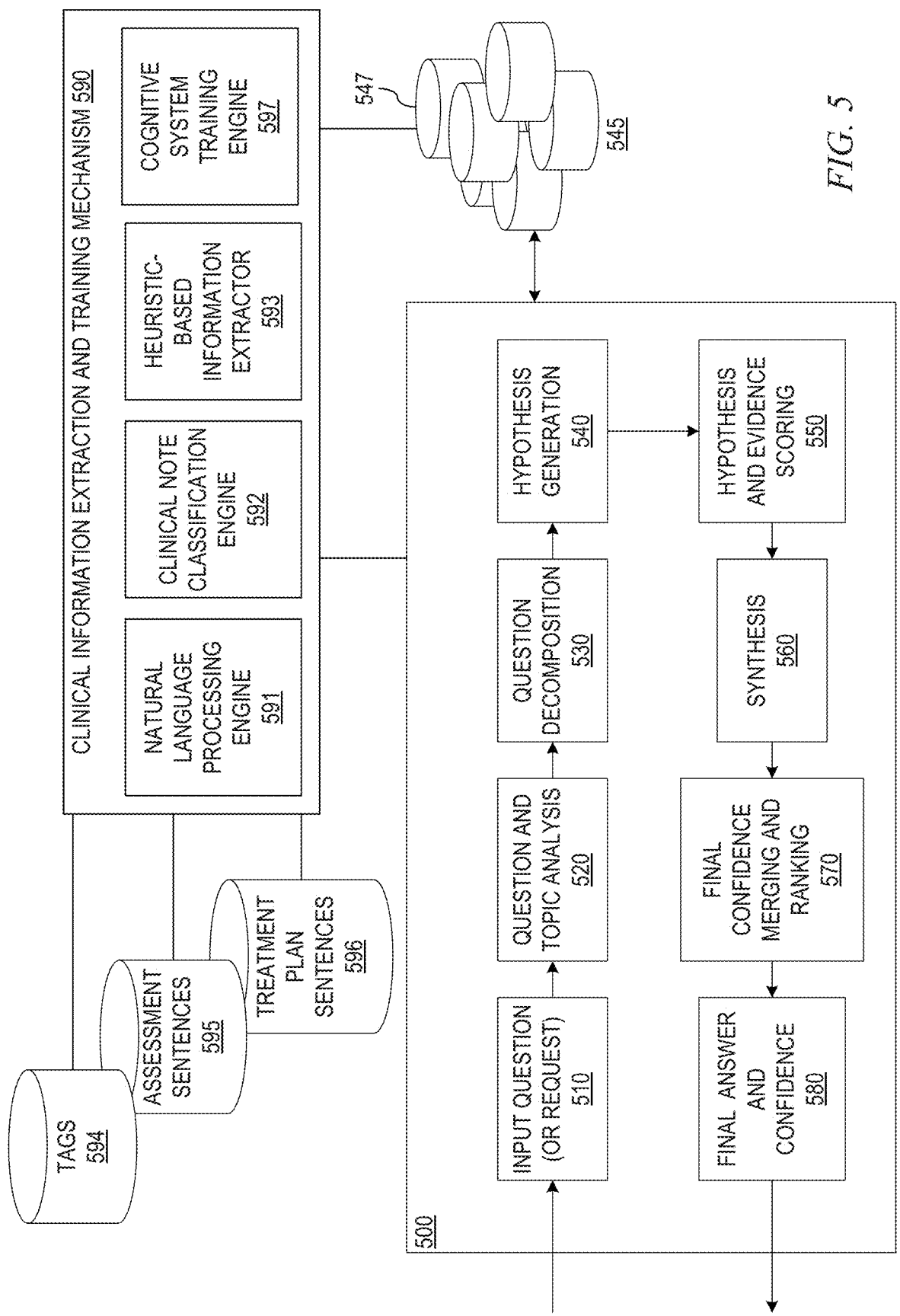
FIG. 5 illustrates a cognitive healthcare system implementing a Question and Answer (QA) or request processing pipeline for processing an input question or request in accordance with one illustrative embodiment.

FIG. 5 illustrates a QA pipeline of a healthcare cognitive system, such as an implementation of cognitive system 100 in FIG. 1, for processing input questions in accordance with one illustrative embodiment. It should be appreciated that the stages of the QA pipeline shown in FIG. 5 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA pipeline of FIG. 5 is augmented, for example, in one or more of the stages to implement the improved mechanism of the illustrative embodiments described hereafter, additional stages may be provided to implement the improved mechanism, or separate logic from the pipeline 500 may be provided for interfacing with the pipeline 500 and implementing the improved functionality and operations of the illustrative embodiments.

As shown in FIG. 5, the QA pipeline 500 comprises a plurality of stages 510-580 through which the cognitive system operates to analyze an input question and generate a final response. In an initial question input stage 510, the QA pipeline 500 receives an input question that is presented in a natural language format. That is, a user inputs, via a user interface, an input question for which the user wishes to obtain an answer, e.g., "What medical treatments for diabetes are applicable to a 60 year old patient with cardiac disease?" In response to receiving the input question, the next stage of the QA pipeline 500, i.e. the question and topic analysis stage 520, parses the input question using natural language processing (NLP) techniques to extract major features from the input question, and classify the major features according to types, e.g., names, dates, or any of a plethora of other defined topics. For example, in a question of the type "Who were Washington's closest advisors?", the term "who" may be associated with a topic for "persons" indicating that the identity of a person is being sought, "Washington" may be identified as a proper name of a person with Which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient in addition, the extracted major features include key words and phrases, classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500 s to speed up the game and involves two pieces of the same color?," the LAT is the string "maneuver," The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 5, the identified major features are then used during the question decomposition stage 530 to decompose the question into one or more queries that are applied to the corpora of data/information 545 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 545, That is, these various sources themselves, different collections of sources, and the like, represent a different corpus 547 within the corpora 545. There may be different corpora 547 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 547 within the corpora 545.

The queries are applied to one or more databases storing information about the electronic texts, documents, articles, websites, and the like, that make up the corpus of data/information, e.g., the corpus of data 106 in FIG. 1. The queries are applied to the corpus of data/information at the hypothesis generation stage 540 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 540, to generate hypotheses for answering the input question. These hypotheses are also referred to herein as "candidate answers" for the input question. For any input question, at this stage 540, there may be hundreds of hypotheses or candidate answers generated that may need to be evaluated.

The QA pipeline 500, in stage 550, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs Which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than tower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but stilt higher than a synonym of the type "film" or "moving picture show." Instances of the exact matches and synonyms for each evidence passage may be compiled and used in a quantitative function to generate a score for the degree of matching of the evidence passage to the input question, Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that, this is just one simple example of how scoring can be performed. Many other algorithms of various complexity may be used to generate scores for candidate answers and evidence without departing from the spirit and scope of the present invention.

In the synthesis stage 560, the large numbers of scores generated by the various reasoning algorithms are synthesized into confidence scores or confidence measures for the various hypotheses. This process involves applying weights to the various scores, where the weights have been determined through training of the statistical model employed by the QA pipeline 500 and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 500 that identifies a manner by which these scores may be combined to generate a confidence score or measure for the individual hypotheses or candidate answers. This confidence score or measure summarizes the level of confidence that the QA pipeline 500 has about the evidence that the candidate answer is inferred by the input question, i.e. that the candidate answer is the correct answer for the input question.

The resulting confidence scores or measures are processed by a final confidence merging and ranking stage 570 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 580, a final answer and confidence score, or final set of candidate answers and confidence scores, are generated and output to the submitter of the original input question via a graphical user interface or other mechanism for outputting information.

As shown in FIG. 5, in accordance with one illustrative embodiment, QA pipeline 500 is further augmented, in accordance with the mechanisms of the illustrative embodiments, to include logic implemented in specialized hardware, software executed on hardware, or any combination of specialized hardware and software executed on hardware, for implementing a clinical information extraction and training mechanism for training supervised machine learning models to automatically extract and identify information in plain text narratives of electronic medical records. Clinical information extraction and training mechanism 590 comprises natural language processing engine 591, clinical note classification engine 592, heuristic-based information extractor 593, and cognitive system training engine 597.

In order to initially train QA pipeline 500 to identify and extract information in plain text narratives of electronic medical records (EMRs), such as those in a corpus 547 within the corpora 545, natural language processing engine 591 performs natural language processing, such as sentence segmentation, tokenization, parts-of-speech tagging, parsing, or the like, on the text within each clinical note associated with the EMRs of patients within a corpus 547 within the corpora 545 so as to link terms in the clinical notes to concepts in language data such as the Unified Medical Language System (UMLS).

Clinical note classification engine 592 then segments the clinical notes into sections and labels each section in a set of sequential steps using one or more different supervised machine learning models. Initially, a section-header identification (supervised learning) model predicts whether a given sentence is the header of a section using several textual and structural features. Subsequently, a section segmentation model segments the clinical note into contiguous blocks of sentences using conditional random fields. The section segmentation model uses predictions from the section-header identifier as a feature. Finally, a section labeler model performs a supervised multi-label classification to assign section labels to the segmented blocks of text.

Heuristic-based information extractor 593 then operates on the sections identified by clinical note classification engine 592. Heuristic-based information extractor 593 utilizes a set of patterns and rules to determine a potential start and a potential end of an explicitly tagged sequence of sentences. The illustrative embodiments consider a contiguous block of sentences as a section, i.e. an assessment section, a treatment plan section, or the like. To develop the set of patterns and rules, heuristic-based information extractor 593 inspects a corpus 547 within the corpora 545 to identify frequently occurring section headings, such as "Assessment," "A," "Plan," "P," "Recommendation," "Instruction," or the like. Heuristic-based information extractor 593 identifies tags that, when leveraged, yield high precision sentences that serve as positive instances of sentences, i.e. assessment sentences, treatment plan sentences, or the like, for use in identifying assessments, treatment plans, or the like, that occur in clinical notes but fait to have identifying tags, Heuristic-based information extractor 593 adds the identified tags to tag data structure 594.

Utilizing tag data structure 594, heuristic-based information extractor 593 performs statistical analysis of all clinical note sections of the clinical notes that contain tags identified in tag data structure 594 to identify one or more valid stop/start conditions. The sections are typically expressed on a malady basis, starting with, for example, a set of assessment sentences followed by a set of treatment plan sentences, which were often written as a list. Therefore, at the end of such a list, the start of another section may be identified by a section heading of a new malady, a start of a new section identified by clinical note classification engine 592, or a presence of one or more blank lines identifying a robust stop/start condition.

Thus, utilizing the tags in tag data structure 594 as well as the one or more valid stop/start conditions, heuristic-based information extractor 593 extracts positive examples of sentences for different types of information. For example, for assessments within the clinical notes, heuristic-based information extractor 593 identifies assessments sections of the clinical notes identified with an assessment tag, such as "Assessment," "A," or the like. Heuristic-based information extractor 593 extracts the sentences associated with such assessment tags and stores them as positive examples of assessment sentences in assessment sentence data structure 595. As another example, for treatment plans in the clinical notes, heuristic-based information extractor 593 identifies treatment plan sections of the clinical notes identified with a treatment plan tag, s such as "Plan," "P," "Recommendation," "Instruction," or the like. Heuristic-based information extractor 593 extracts the sentences associated with such treatment plan tags and stores them as positive examples of treatment plan sentences in sentence data structure 596. In the illustrative embodiments, while assessment sentences in assessment sentence data structure 595 are examples of positive assessment sentences, these assessment sentences may also be utilized as examples of negative treatment plan sentences. That is, as will be discussed in detail hereafter, in training QA pipeline 500 to identify treatment plans that fail to have an associated treatment plan tag, heuristic-based information extractor 593 may utilize those assessment sentences in assessment sentence data structure 595 as negative examples when identifying treatment plan sentences that fail to have an associated treatment plan tag. It should be noted that heuristic-based information extractor 593 may identify other examples of non-treatment plan sentences in clinical notes, such as those that come from other sections that are identified by other tags associated with other non-treatment plan sections. Heuristic-based information extractor 593 may store these other examples in a different data structure, Which is not illustrated in FIG. 1.

With both positive and negative examples of information sentences identified based on associated tags, cognitive system training engine 597 then utilizes the positive and negative examples of information sentences to train QA pipeline 500 to classify sentences within clinical notes of the EMRs in a corpus 547 within the corpora 545 that are identified by tags as well as those that fail to have an associated tag. As one example, cognitive system training engine 597 may be used to classify treatment plan sentences within the clinical notes of the EMRs of a selected patient that are identified by treatment plan tags, such as "Plan," "P," "Recommendation," "Instruction," or the like, as well as those treatment plan sentences that fail to have an associated treatment plan tag. A treatment plan is a therapeutic strategy detailing the treatment to be provided and expected outcome, patient goals, dietary adjustment, an exercise program or expected duration of the treatment prescribed by the clinician, such as a physician, physician assistant, nurse, or the like. Treatment plans are especially important in the optimal management of complex or chronic illnesses, Therefore, identifying each and every treatment plan for the selected patient is important when continuing the healthcare of the patient.

Thus, cognitive system training engine 597 trains QA pipeline 500 to classify sentences within clinical notes of the EMRs in a corpus 547 within the corpora 545 identified by NLP engine 591 utilizing machine learning features such as Support Vector Machines (SVM), Convolutional Neural Networks (CNN), or the like, for identification and classification of sentences within clinical notes of the EMRs in a corpus 547 within the corpora 545.

Utilizing Support Vector Machines, cognitive system training engine 597 sentences train QA pipeline 500 to classify sentences not identified by the selected set of tags using the positive examples of the selected information sentences, negative examples of the non-selected information sentences and one or more of the following:

Bag-of-words: A sentence was represented as a set of words and all words in the sentence were lemmatized, i.e. the words of the sentence grouping inflected or variant forms of the same word.

Syntactic n-gram features: Using a medical domain-adapted English Slot Grammar parser to obtain a dependency based syntactic tree for the sentences. Based on the dependency-parse tree provided by the parser, obtaining possible paths of lengths, 2, 3, 4 and include them as features.

Medical concepts: Identify Unified Medical Language System (UMLS) concepts (Concept Unique Identifiers) in a sentence as features.

Morpho-syntactic features of the verbs: Identify features derived from the morpho-syntactic properties of verbs in the sentences. The primary properties and distinctions included the position of the verb (i.e. head of a main clause or an auxiliary, which marks tense and aspect) and the tense markings themselves (past, present or future). Features considered important in identifying treatment plan sentences as they are typically expressed using future tense or imperative verbs. (Example: The patient will be sent for an MRI to further evaluate the knee). On the other hand, an assessment sentences are typically written using past tense verbs. (Example: The patient was able to go through PT but at a much slower pace).

Assertions: Identify clinical assertions on medical concepts. Specifically, adding negated and hypothetical assertions on clinical concepts as features. Features considered useful as disease assessments often have negations. (Example: No significant changes since the prior exam). Whereas, treatment plans often contain hypotheticals (Example: Call back if symptoms persist or worsen)

Sentence Length: information, such as treatment plans, are expressed as multiple short sentences.

Global Features: Utilizing section-labels identified using note section classifiers (introduced earlier), note type (progress note, discharge note etc.), note category (primary care, test reports, specialty category etc.), and provider type (physician, social worker, registered nurse practitioner etc.) as features.

Therefore, cognitive system training engine 597 trains QA pipeline 500 to classify sentences not identified by the selected set of tags using the positive examples of the selected information sentences, negative examples of the non-selected information sentences and one or more of these features. However, the illustrative embodiments may decide which of the features to use in training QA pipeline 500 using a statistical feature selection technique, such as Pointwise Mutual Information (PMI), Fisher exact test, or the like.

Cognitive system training engine 597 may also use convolutional neural networks (CNN) that utilizes layers with convolving filters that are applied to local features. In the use of CNN, an embedding layer maps every word with its corresponding low dimensional feature vector. Word vectors may be randomly initialized the embedding layer or initialized with word vectors obtained by training an unsupervised neural language model on a large domain-dependent corpus is effective. In the convolutional neural network architecture, the embedding layer is followed by a convolution layer of different filter sizes, a 1-max pooling layer, a fully connected feed forward neural network layer, and a softmax classifier as the output layer. Global features' embeddings are then concatenated with the outputs of max-pool layer from the word-level inputs. It is worth noting that global features are not at word-level but at sentence-level and they are not sequential like words, thus are not feed in directly at the word-level input layer.

Thus, cognitive system training engine 597 may train QA pipeline 500 using convolutional neural networks, such as one or more of:

Utilizing randomly initialized word vectors in the embedding layer.

Utilizing pre-trained word vectors from various articles.

Utilizing pre-trained word vectors from the patients EMRs.

Utilizing pre-trained word vectors from various articles, pre-trained word vectors from the patients EMRs, and selected global features.

Thus, cognitive system training engine 597 trains QA pipeline 500 using convolutional neural networks where augment word level features are initialized using pre-trained embeddings and global features initialized using random embedding's in a novel architecture. This word level embeddings and global embedding's are concatenated after the max-pool layer from the word-level inputs. It is worth noting that global features are not at word-level but at sentence-level and they are not sequential unlike words and thus, cannot be feed directly at the word-level input layer.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the users computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider), in some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
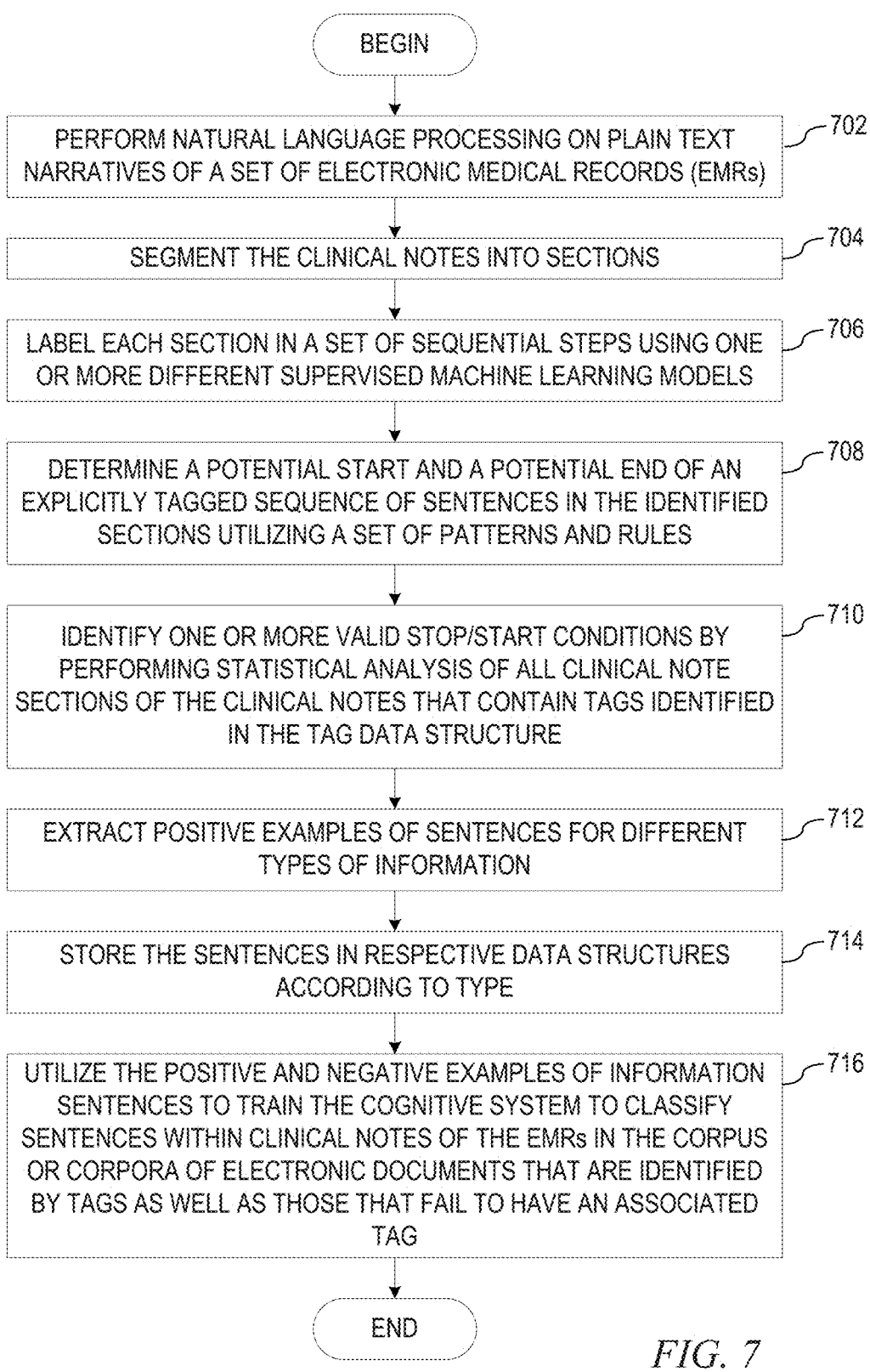
FIG. 7 depicts a flowchart of the operation performed by a clinical information extraction and training mechanism for training supervised machine learning models to automatically extract and identify information in plain text narratives of electronic medical records in accordance with an illustrative embodiment.

FIG. 7 depicts a flowchart of the operation performed by a clinical information extraction and training mechanism for training supervised machine learning models to automatically extract and identify information in plain text narratives of electronic medical records in accordance with an illustrative embodiment. As the operation begins, the clinical information extraction and training mechanism performs natural language processing on plain text narratives of a set of electronic medical records (EMRs) (step 702). The natural language processing may include one or more of sentence segmentation, tokenization, parts-of-speech tagging, parsing, or the like, so as to link terms in the clinical notes to concepts in language data such as the Unified Medical Language System (UMLS).

The clinical information extraction and training mechanism then segments the clinical notes into sections (step 704) and labels each section in a set of sequential steps using one or more different supervised machine learning models (step 706). Initially, a section-header identification. (supervised learning) model predicts whether a given sentence is the header of a section using several textual and structural features. Subsequently, a section segmentation model segments the clinical note into contiguous blocks of sentences using conditional random fields. The section segmentation model uses predictions from the section-header identifier as a feature. Finally, a section labeler model performs a supervised multi-label classification to assign section labels to the segmented blocks of text.

The clinical information extraction and training mechanism then operates on the identified sections utilizing a set of patterns and rules to determine a potential start and a potential end of an explicitly tagged sequence of sentences (step 708). The illustrative embodiments consider a contiguous block of sentences as a section, i.e. an assessment section, a treatment plan section, or the like. To develop the set of patterns and rules, the clinical information extraction and training mechanism inspects a corpus or corpora of electronic documents to identify frequently occurring section headings, such as "Assessment," "A," "Plan," "P," "Recommendation," "Instruction," or the like. The clinical information extraction and training mechanism identifies tags that, when leveraged, yield high precision sentences that serve as positive instances of sentences, i.e. assessment sentences, treatment plan sentences, or the like, for use in identifying assessments, treatment plans, or the like, that occur in clinical notes but fail to have identifying tags. The clinical information extraction and training mechanism adds the identified tags to a tag data structure.

Utilizing the tag data structure, the clinical information extraction and training mechanism performs statistical analysis of all clinical note sections of the clinical notes that contain tags identified in the tag data structure to identify one or more valid stop/start conditions step 710). The sections are typically expressed on a malady basis, starting with, for example, a set of assessment sentences followed by a set of treatment plan sentences, which were often written as a list. Therefore, at the end of such a list, the start of another section may be identified by a section heading of a new malady, a start of a new section previously identified, or a presence of one or more blank lines identifying a robust stop/start condition.

Utilizing the tags in the tag data structure as well as the one or more valid stop/start conditions, the clinical information extraction and training mechanism extracts positive examples of sentences for different types of information (step 712) and stores the sentences in respective data structures according to type (step 714). In the illustrative embodiments, one data structure comprising a first type of sentences may be utilized as positive instances of sentences when extracting sentences associated with the first type from clinical notes while another data structure of second type may be utilized as negative instances of sentences when extracting sentences associated with the first type from clinical notes.

With both positive and negative examples of information sentences identified based on associated tags, the clinical information extraction and training mechanism then utilizes the positive and negative examples of information sentences to train the cognitive system to classify sentences within clinical notes of the EMRs in the corpus or corpora of electronic documents that are identified by tags as well as those that fail to have an associated tag (step 716). The clinical information extraction and training mechanism may train the cognitive system to classify identified sentences within clinical notes of the EMRs in the corpus or corpora of electronic documents utilizing machine learning features such as Support Vector Machines (SVM), Convolutional Neural Networks (CNN), or the like, for identification and classification of sentences within clinical notes of the EMRs in the corpus or corpora of electronic documents. The operation ends thereafter.

Thus, the illustrative embodiments provide mechanisms for automatically generating ground truth from clinical notes to identify information in the clinical notes, such as assessments, treatment plans, or the like. The tagged sections serve as a source of high precision training data because the tag and simple additional rules may be leveraged to extract the sentences within the scope of the tag. These extracted sentences may be used as positive and negative instances to train a supervised machine learning model, which are later utilized to recognize sentences belonging to the same category occurring without the tag elsewhere in the same clinical note or in other clinical notes.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, for training, a machine learning computer model, the method comprising:
    segmenting each clinical note, in a plurality of clinical notes, of a corpus of electronic medical records, into one or more corresponding identified sections using natural language processed plain text narratives of the plurality of clinical notes;
    for each clinical note, labeling each corresponding identified section, in the one or more corresponding identified sections, with at least one associated tag, wherein labeling comprises executing one or more machine learning computer models that process each corresponding identified section to segment the clinical note into blocks of sentences and perform a multi-label classification operation to associate a tag with one or more of the blocks of sentences, wherein the tag is metadata that specifies a label from a plurality of predetermined labels that corresponds to the block of sentences;
    generating a tag data structure based on the tagged blocks of sentences and associated tags of the blocks of sentences;
    performing statistical analysis of the identified sections in the plurality of clinical notes that contain tags identified in the tag data structure to identify one or more valid stop/start conditions utilizing the tag data structure;
    extracting a first set of examples of sentences for a first selected type of information corresponding to associated tags in the tag data structure and the one or more valid stop/start conditions; and
    training, via a machine learning training operation, a sentence classification machine learning computer model of a cognitive computing system to identify classify sentences in the plurality of clinical notes based on the first selected type of information, wherein classifying the sentences comprises classifying sentences that fail to have a tag associated with the first selected type of information, and wherein the training inputs the first set of examples of sentences for different types of information as positive example training input data, and trains the sentence classification machine learning computer model to classify sentences in clinical notes of electronic medical records based on the positive example training input data.

2. The method of claim 1, further comprising:
    extracting a second set of examples of sentences for a second selected type of information corresponding to associated tags in the tag data structure and the one or more valid stop/start conditions; and
    further training, via the machine learning training operation, the machine learning computer model of the cognitive system to classify sentences in the plurality of clinical notes based on the second selected type of information, wherein classifying sentences comprises classifying sentences that have a tag associated with the second selected type, and wherein the training inputs the examples of sentences for the second selected type of information as negative example training input data.

3. The method of claim 1, wherein the one or more machine learning computer models that process each corresponding identified section comprises a plurality of different supervised machine learning computer models including:
    a section-header identification machine learning computer model that processes one or more sentences of the corresponding identified section and predicts whether a given sentence is the header of the identified section using textual and structural features;
    a section segmentation machine learning computer model that segments the clinical note into the blocks of sentences using conditional random fields; and
    a section labeler machine learning computer model that performs the multi-label classification operation to assign the associated tag to the one or more blocks of sentences based on a textual pattern recognition operation of the section labeler machine learning computer model.

4. The method of claim 1, further comprising
    determining a potential start and a potential end of an explicitly tagged sequence of sentences using a set of patterns and rules.

5. The method of claim 4, wherein the set of patterns and rules are developed by:

inspecting a corpus or corpora of electronic documents to identify frequently occurring section headings; and identifying tags that, when leveraged, yield high precision sentences that serve as positive instances of sentences.

6. The method of claim 1, wherein the machine learning computer model of the cognitive system comprises at least one of a support vector machine or a convolutional neural network.

7. A computer program product comprising a computer readable storage medium having a computer readable program stored therein, wherein the computer readable program, when executed on a computing device, causes the computing device to:

segment each clinical note, in a plurality of clinical notes, of a corpus of electronic medical records, into one or more corresponding identified sections using natural language processed plain text narratives of the plurality of clinical notes;

for each clinical note label each corresponding identified section, in the one or more corresponding identified sections, with at least one associated tag, wherein labeling comprises executing one or more machine learning computer models that process each corresponding identified section to segment, the clinical note into blocks of sentences and perform a multi-label classification operation to associate a tag with one or more of the blocks of sentences, wherein the tag is metadata that specifies a label from a plurality of predetermined labels that corresponds to the block of sentences;

generate a tag data structure based on the tagged blocks of sentences and associated tags of the blocks of sentences;

perform statistical analysis of the identified sections in the plurality of clinical notes that contain tags identified in the tag data structure to identify one or more valid stop/start conditions utilizing the tag data structure;

extract a first set of examples of sentences for a first selected type of information corresponding to associated tags in the tag data structure and the one or more valid stop/start conditions; and train, via a machine learning training operation, a sentence classification machine learning computer model of a cognitive computing system to classify sentences in the plurality of clinical notes based on the first selected type of information, wherein classifying the sentences comprises classifying sentences that fail to have a tag associated with the first selected type of information, and wherein the training inputs the first set of examples of sentences for different types of information as positive example training input data, and trains the sentence classification machine learning computer model to classify sentences in clinical notes of electronic medical records based on the positive example training input data.

8. The computer program product of claim 7, wherein the computer readable program further causes the computing device to:

extract a second set of examples of sentences for a second selected type of information corresponding to associated tags in the tag data structure and the one or more valid stop/start conditions; and further train, via the machine learning training operation, the machine learning computer model of the cognitive system to classify sentences in the plurality of clinical notes based on the second selected type of information, wherein classifying sentences comprises classifying sentences that have a tag associated with the second selected type, and wherein the training inputs the examples of sentences for the second selected type of information as negative example training input data.

9. The computer program product of claim 7, wherein the one or more machine learning computer models that process each corresponding identified section comprises a plurality of different supervised machine learning computer models including:

a section-header identification machine learning computer model that processes one or more sentences of the corresponding identified section and predicts whether a given sentence is the header of the identified section using textual and structural features;

a section segmentation machine learning computer model that segments the clinical note into the blocks of sentences using conditional random fields; and a section labeler machine learning computer model that performs the multi-label classification operation to assign the associated tag to the one or more blocks of sentences based on a textual pattern recognition operation of the section labeler machine learning computer model.

10. The computer program product of claim 7, wherein the computer readable program further causes the computing device to:

determine a potential start and a potential end of an explicitly tagged sequence of sentences using a set of patterns and rules.

11. The computer program product of claim 10, wherein the computer readable program to develop the set of patterns and rules further causes the computing device to:

inspect a corpus or corpora of electronic documents to identify frequently occurring section headings; and identify tags that, when leveraged, yield high precision sentences that serve as positive instances of sentences.

12. The computer program product of claim 7, wherein the machine learning computer model of the cognitive system comprises at least one of a support vector machine or a convolutional neural network.

13. An apparatus comprising:

a processor; and a memory coupled to the processor, wherein the memory comprises instructions which, when executed by the processor, cause the processor to implement a clinical information extraction and training mechanism for automatically extracting and identifying information in plain text narratives in a set of electronic medical records, wherein the clinical information extraction and training mechanism operates to:

segment each clinical note, in a plurality of clinical notes, of a corpus of electronic medical records, into one or more corresponding identified sections using natural language processed plain text narratives of the plurality of clinical notes;

for each clinical note, label each corresponding identified section, in the one or more corresponding identified sections, with at least one associated tag, wherein labeling comprises executing one or more machine learning computer models that process each corresponding identified section to segment the clinical note into blocks of sentences and perform a multi-label classification operation to associate a tag with one or more of the blocks of sentences, wherein the tag is metadata, that specifies a label from a plurality of predetermined labels that corresponds to the block of sentences;

generate a tag data structure based on the tagged blocks of sentences and associated tags of the blocks of sentences;

perform statistical analysis of the identified sections in the plurality of clinical notes that contain tags identified in the tag data structure to identify one or more valid stop/start conditions utilizing the tag data structure;

extract a first set of examples of sentences for a first selected type of information corresponding to associated tags in the tag data structure and the one or more valid stop/start conditions; and train, via a machine learning training operation, a sentence classification machine learning computer model of a cognitive computing system to classify sentences in the plurality of clinical notes based on the first selected type of information, wherein, classifying the sentences comprises classifying sentences that fail to have a tag associated with the first selected type of information, and wherein the training inputs the first set of examples of sentences for different types of information as positive example training input data, and trains the sentence classification machine learning computer model to classify sentences in clinical notes of electronic medical records based on the positive example training input data.

14. The apparatus of claim 13, wherein the instructions further cause the processor to:

extract a second set of examples of sentences for a second selected type of information corresponding to associated tags in the tag data structure and the one or more valid stop/start conditions; and further train, via the machine learning training operation, the machine learning computer model of the cognitive system to classify sentences in the plurality of clinical notes based on the second selected type of information, wherein classifying sentences comprises classifying sentences that have a tag associated with the second selected type, and wherein the training inputs the examples of sentences for the second selected type of information as negative example training input data.

15. The apparatus of claim 13, wherein the one or more machine learning computer models that process each corresponding identified section comprises a plurality of different supervised machine learning computer models including;

a section-header identification machine learning computer model that processes one or more sentences of the corresponding identified section and predicts whether a given sentence is the header of the identified section using textual and structural features;

a section segmentation machine learning computer model that segments the clinical note into the blocks of sentences using conditional random fields; and a section labeler machine learning computer model that performs the multi-label classification operation to assign the associated tag to the one or more blocks of sentences basal on a textual pattern recognition operation of the section labeler machine learning computer model.

16. The apparatus of claim 13, wherein the instructions further cause the processor to:

determine a potential start and a potential end of an explicitly tagged sequence of sentences using a set of patterns and rules.

17. The apparatus of claim 16, wherein the instructions to develop the set of patterns and rules further cause the processor to:

inspect a corpus or corpora of electronic documents to identify frequently occurring section headings; and identify tags that, when leveraged, yield high precision sentences that serve as positive instances of sentences.

18. The apparatus of claim 13, wherein the machine learning computer model of the cognitive system comprises at least one of a support vector machine or convolutional neural network.

19. The method of claim 1, wherein the machine learning computer model of the cognitive computing system is trained to classify clinical notes of the electronic medical records that do not have associated treatment plan tags with patterns of sentences that correspond to one or more sections of a treatment plan, and to associate corresponding treatment plan tags of the one or more sections of the treatment plan with the clinical notes of the electronic medical records.

20. The method of claim 19, further comprising:

executing the trained machine learning computer model of the cognitive computing system to classify the clinical notes of the electronic medical records and associate treatment plan tags with the clinical notes to generate tagged clinical notes; and perform, by the cognitive computing system, a question answering cognitive computing operation based on the treatment plan tags associated with the clinical notes of the electronic medical records that answers input questions by automatically identifying candidate answers to the input questions based on the tagged clinical notes.

* * * * *